(12) United States Patent  
Inukai et al.

(10) Patent No.: US 6,500,127 B1
(45) Date of Patent: Dec. 31, 2002

(54) BLOOD PRESSURE MONITOR APPARATUS

(75) Inventors: Hidekatsu Inukai, Nagoya (JP); Keizoh Kawaguchi, Komaki (JP); Akihiro Yokozeki, Komaki (JP)

(73) Assignee: Colin Corporation, Komaki (JP)

( * ) Notice: Subject to any disclaimer, the term of this patent is extended or adjusted under 35 U.S.C. 154(b) by 0 days.

(21) Appl. No.: 09/569,240

(22) Filed: May 11, 2000

(51) Int. Cl.[7] .................................................. A61B 5/00
(52) U.S. Cl. ....................................... 600/485; 600/500
(58) Field of Search ................................ 600/481, 485, 600/490, 493–496, 500

(56) References Cited

U.S. PATENT DOCUMENTS

| | | | | |
|---|---|---|---|---|
| 4,915,103 A | * | 4/1990 | Visveshwara | 128/204.23 |
| 5,564,427 A | * | 10/1996 | Aso et al. | 600/500 |
| 5,752,920 A | * | 5/1998 | Ogura et al. | 600/494 |
| 5,868,679 A | * | 2/1999 | Miyazaki | 600/494 |
| 6,036,652 A | * | 3/2000 | Inukai et al. | 600/500 |
| 6,083,171 A | * | 7/2000 | Ono et al. | 600/494 |
| 6,190,325 B1 | * | 2/2001 | Narimatsu | 600/490 |
| 6,196,974 B1 | * | 3/2001 | Miwa | 600/494 |

FOREIGN PATENT DOCUMENTS

| | | |
|---|---|---|
| CH | 557 671 A | 1/1975 |
| EP | 0 123 313 A2 | 10/1984 |
| EP | 0 804 899 A1 | 11/1997 |
| WO | WO 92/03967 A2 | 3/1992 |

\* cited by examiner

*Primary Examiner*—Robert L. Nasser
(74) *Attorney, Agent, or Firm*—Oliff & Berridge, PLC

(57) ABSTRACT

A blood pressure monitor apparatus for monitoring a blood pressure of a living subject, comprising: blood pressure-relating information obtaining means for successively obtaining blood pressure-relating information which decreases or increases with a decrease or an increase of the blood pressure of the subject, or blood pressure-relating information which increases or decreases with a decrease or an increase of the blood pressure of the subject; decrease or increase determining means for determining a decrease or an increase of the blood pressure-relating information successively obtained by the obtaining means; and abnormality judging means for judging that the blood pressure of the subject is abnormal when the decrease or increase of the blood pressure-relating information is greater than a predetermined reference value ($\gamma_1$, $\gamma_2$), or abnormality judging means for judging that the blood pressure of the subject is abnormal when the blood pressure-relating information is greater than a predetermined reference value ($TH_H$) or smaller than a predetermined reference value ($TH_L$).

20 Claims, 10 Drawing Sheets

BLOOD PRESSURE MONITOR APPARATUS

The present application is based on Japanese Patent Application No. 10-337696 filed Nov. 27, 1998, the contents of which are incorporated hereinto by reference.

BACKGROUND OF THE INVENTION

1. Field of the Invention

The present invention relates to a blood pressure monitor apparatus which monitors a blood pressure of a living subject based on blood pressure-relating information which changes with a change of the blood pressure of the subject.

2. Discussion of the Related Art

There has been proposed a blood pressure monitor apparatus which successively obtains blood pressure-relating information of a living subject (patient) and judges abnormality of the blood pressure when the blood pressure-relating information is greater than a predetermined upper reference value or smaller than a predetermined lower reference value. The blood pressure-relating information includes a blood pressure which is measured by using a catheter or a cuff, pulse-wave propagation velocity-relating information such as a pulse-wave propagation velocity at which a pulse wave propagates through an artery or a pulse-wave propagation time during which a pulse wave propagates between predetermined two portions of an artery, heart rate-relating information such as a heart rate or a pulse period which changes due to conditions of a central organ (heart) of the subject, peripheral blood volume-relating information such as a peripheral pulse-wave area which indicates a peripheral blood volume and which changes due to conditions of a peripheral organ (blood vessels) of the subject, and blood oxygen saturation. The above-indicated conventional blood pressure monitor apparatus which monitors the blood pressure-relating information automatically determines abnormality of the blood pressure of the subject based on the obtained blood pressure-relating information, so that the abnormal condition of the patient can be quickly dealt with.

The conventional blood pressure monitor apparatus determines abnormality of the blood pressure of the patient when the detected or obtained blood pressure-relating information is greater than a predetermined upper reference value or smaller than a predetermined lower reference value. Accordingly, the conventional blood pressure monitor apparatus equally determines abnormality of the blood pressure due to an abrupt change thereof in a considerably short period of time and due to a gradual change thereof in a relatively long period of time. In general, the abnormal condition of the patient detected when the blood pressure-relating information has abruptly changed should be dealt with as quickly as possible, as compared with that detected when the blood pressure-relating information has gradually changed. The conventional apparatus described above, however, cannot assure that a suitable medical treatment is given without delay on the patient whose blood pressure-relating information has abruptly changed.

SUMMARY OF THE INVENTION

It is therefore an object of the present invention to provide a blood pressure monitor apparatus which is capable of quickly detecting abnormality of the blood pressure of a patient when the blood pressure has changed abruptly.

The above object may be attained according to a first aspect of the present invention, which provides a blood pressure monitor apparatus for monitoring a blood pressure of a living subject, comprising: blood pressure-relating information obtaining means for successively obtaining blood pressure-relating information which decreases with a decrease of the blood pressure of the subject; decrease determining means for determining a decrease of the blood pressure-relating information successively obtained by the obtaining means; and abnormality judging means for judging that the blood pressure of the subject is abnormal when the decrease of the blood pressure-relating information is greater than a predetermined reference value ($\gamma_1$).

The above object may also be attained according to a second aspect of the present invention, which provides a blood pressure monitor apparatus for monitoring a blood pressure of a living subject, comprising: blood pressure-relating information obtaining means for successively obtaining blood pressure-relating information which increases with a increase of the blood pressure of the subject; increase determining means for determining an increase of the blood pressure-relating information successively obtained by the obtaining means; and abnormality judging means for judging that the blood pressure of the subject is abnormal when the increase of the blood pressure-relating information is greater than a predetermined reference value ($\gamma_2$).

The above object may also be attained according to a third aspect of the present invention, which provides a blood pressure monitor apparatus for monitoring a blood pressure of a living subject, comprising: blood pressure-relating information obtaining means for successively obtaining blood pressure-relating information which decreases with an increase of the blood pressure of the subject; decrease determining means for determining a decrease of the blood pressure-relating information successively obtained by the obtaining means; and abnormality judging means for judging that the blood pressure of the subject is abnormal when the decrease of the blood pressure-relating information is greater than a predetermined reference value ($\gamma_2$).

The above object may also be attained according to a fourth aspect of the present invention, which provides a blood pressure monitor apparatus for monitoring a blood pressure of a living subject, comprising: blood pressure-relating information obtaining means for successively obtaining blood pressure-relating information which increases with a decrease of the blood pressure of the subject; increase determining means for determining an increase of the blood pressure-relating information successively obtained by the obtaining means; and abnormality judging means for judging that the blood pressure of the subject is abnormal when the increase of the blood pressure-relating information is greater than a predetermined reference value ($\gamma_1$).

In the blood pressure monitor apparatuses constructed as described above, the decrease or increase determining means determines a decrease or an increase of the blood pressure-relating information successively obtained by the blood pressure-relating information obtaining means, and the abnormality judging means judges that the blood pressure of the living subject (patient) is abnormal when the decrease or increase of the blood pressure-relating information is greater than the predetermined reference value. In other words, when the blood pressure-relating information has abruptly decreased or increased, the abnormality judging means judges that the blood pressure of the patient is abnormal even if the blood pressure-relating information may be normal or permissible. Accordingly, the abnormality of the blood pressure of the patient can be detected without delay when the blood pressure has abruptly decreased or increased.

In a preferred form of the above first or fourth aspect of the present invention, the blood pressure monitor apparatus further comprises reference value determining means for determining the reference value ($\gamma_1$) based on the blood pressure-relating information successively obtained by the obtaining means, by utilizing a predetermined relationship between reference value and blood pressure-relating information, the relationship being predetermined such that a smaller reference value corresponds to blood pressure-relating information corresponding to a lower blood pressure.

According to the above preferred form of the first or fourth aspect of the invention, the reference value determining means determines the reference value ($\gamma_1$) which is used in judging the abnormality of the blood pressure of the patient by the abnormality judging means, such that a smaller reference value corresponds to blood pressure-relating information corresponding to a lower blood pressure. According to this arrangement, when the blood pressure of the patient is relatively low, the abnormality judging means judges that the blood pressure of the patient is abnormal even if the decrease or increase of the blood pressure-relating information may be relatively small, so that the abnormality of the blood pressure of the patient can be quickly detected without delay when the blood pressure has abruptly decreased. When the blood pressure of the patient is not so low, the abnormality judging means judges that the blood pressure of the patient is abnormal only when the decrease or increase of the blood pressure-relating information is relatively large, so that the judgment of the abnormality of the blood pressure is prevented when the blood pressure of the patient is not so low. In the case where the abnormality of the blood pressure is determined on the basis of only the decrease or increase of the blood pressure-relating information, the reference value must be set at a small value in an attempt to be able to find an abnormal blood pressure even if the blood pressure may gradually decrease. In this case, however, the blood pressure may unnecessarily be judged to be abnormal when the blood pressure is not so low.

In a preferred form of the above second or third aspect of the invention, the blood pressure monitor apparatus further comprises: reference value determining means for determining the reference value ($\gamma_2$) based on the blood pressure-relating information successively obtained by the obtaining means, by utilizing a predetermined relationship between reference value and blood pressure-relating information, the relationship being predetermined such that a smaller reference value corresponds to blood pressure-relating information corresponding to a higher blood pressure.

According to the above preferred form of the above second or third aspect of the present invention, the reference value determining means determines the reference value ($\gamma_2$) which is used in judging abnormality of the blood pressure of the patient by the abnormality judging means, such that a smaller reference value corresponds to the blood pressure-relating information corresponding to a higher blood pressure. According to this arrangement, when the blood pressure of the patient is relatively high, the abnormality judging means judges that the blood pressure of the patient is abnormal even when the increase or decrease of the blood pressure-relating information may be relatively small, so that the abnormality of the blood pressure of the patient can be quickly detected without delay when the blood pressure has abruptly increased. In contrast, when the blood pressure of the patient is not so high, the abnormality judging means judges that the blood pressure of the patient is abnormal only when the increase or decrease of the blood pressure-relating information is relatively large, so that the determination of the abnormality of the blood pressure is prevented when the blood pressure of the patient is not so high. In the case where the abnormality of the blood pressure is determined on the basis of only the increase or decrease of the blood pressure-relating information, the reference value must be set at a small value in an attempt to be able to find an abnormal blood pressure of the patient even when the blood pressure may gradually increase. In this case, however, the blood pressure may unnecessarily be determined to be abnormal when the blood pressure is not so high.

In a preferred form of the above first or third aspect of the invention, the decrease is selected from the group consisting of an amount of decrease of the blood pressure-relating information and a rate of decrease of the blood pressure-relating information.

In a preferred form of the above second or fourth aspect of the invention, the increase is selected from the group consisting of an amount of increase of the blood pressure-relating information and a rate of increase of the blood pressure-relating information.

In a preferred form of the above first or second aspect of the invention, the blood pressure-relating information is selected from the group consisting of an estimated blood-pressure (EBP), a normalizedpulse-wave area ($S_F$), and a pulse-wave propagating velocity ($V_M$).

In a preferred form of the above third or fourth aspect of the invention, the blood pressure-relating information comprises a pulse-wave propagation time (DT).

The above-indicated object of the present invention may also be attained according to a fifth aspect of the invention, which provides a blood pressure monitor apparatus for monitoring a blood pressure of a living subject, comprising: blood pressure-relating information obtaining means for successively obtaining blood pressure-relating information which decreases with a decrease of the blood pressure of the subject; abnormality judging means for judging that the blood pressure of the subject is abnormal when the blood pressure-relating information successively obtained by the obtaining means is smaller than a predetermined reference value ($TH_L$); decrease determining means for determining a decrease of the blood pressure-relating information successively obtained by the obtaining means; and reference value determining means for determining the reference value ($TH_L$) based on the decrease of the blood pressure-relating information successively obtained by the obtaining means, by utilizing a predetermined relationship between reference value and decrease of blood pressure-relating information, the relationship being predetermined such that a greater reference value ($TH_L$) corresponds to a greater decrease of blood pressure-relating information.

In the blood pressure monitor apparatus constructed as described above, the reference value determining means determines the reference value $TH_L$ which is used in judging abnormality of the blood pressure of the subject by the abnormality judging means, based on the decrease of the blood pressure-relating information successively obtained by the obtaining means, by utilizing a predetermined relationship between reference value and decrease of the blood pressure-relating information, the relationship being predetermined such that a greater reference value ($TH_L$) corresponds to a greater decrease of the blood pressure-relating information. Further, the abnormality judging means judges that the blood pressure of the subject has abnormally decreased when the blood pressure-relating information obtained by the obtaining means is smaller than the reference value ($TH_L$). According to this arrangement wherein a greater reference value corresponds to a greater decrease of the blood pressure-relating information, the abnormality judging means judges abnormal decrease of the blood pressure of the subject without delay when the blood pressure has abruptly decreased. In addition, since a smaller reference value corresponds to a smaller decrease of the blood pressure-relating information, the present arrangement prevents determination of abnormal decrease of the blood pressure when the blood pressure of the subject is not so low and the blood pressure has gradually decreases.

In a preferred form of the above fifth or sixth aspect of the invention, the blood pressure-relating information is selected from the group consisting of an estimated blood pressure (EBP), a pulse-wave propagation velocity ($V_M$) and a normalized pulse-wave area ($S_F$).

The above-indicated object of the present invention may also be attained according to a sixth aspect of the invention, which provides a blood pressure monitor apparatus for monitoring a blood pressure of a living subject, comprising: blood pressure-relating information obtaining means for successively obtaining blood pressure-relating information which increases with an increase of the blood pressure of the subject; abnormality judging means for judging that the blood pressure of the subject is abnormal when the blood pressure-relating information successively obtained by the obtaining means is greater than a predetermined reference value ($TH_H$); increase determining means (60) for determining an increase of the blood pressure-relating information successively obtained by the obtaining means; and reference value determining means for determining the reference value ($TH_H$) based on the increase of the blood pressure-relating information successively obtained by the obtaining means, by utilizing a predetermined relationship between reference value and increase of blood pressure-relating information, the relationship being predetermined such that a smaller reference value ($TH_H$) corresponds to a greater increase of blood pressure-relating information.

In the blood pressure monitor apparatus constructed as described above, the reference value determining means determines the reference value $TH_H$ which is used in judging abnormality of the blood pressure of the subject by the abnormality judging means, based on the increase of the blood pressure-relating information successively obtained by the obtaining means, by utilizing a predetermined relationship between reference value and increase of the blood pressure-relating information, the relationship being predetermined such that a smaller reference value ($TH_H$) corresponds to a greater increase of the blood pressure-relating information. Further, the abnormality judging means judges that the blood pressure of the subject has abnormally increased when the blood pressure-relating information obtained by the obtaining means is greater than the reference value. According to this arrangement wherein a smaller reference value corresponds to a greater increase of the blood pressure-relating information, the abnormality judging means judges abnormal increase of the blood pressure of the subject without delay when the blood pressure has abruptly increased. In addition, since a greater reference value corresponds to a smaller increase of the blood pressure-relating information, the present arrangement prevents determination of abnormal increase of the blood pressure when the blood pressure of the subject is not so high and the blood pressure gradually increases.

The above-indicated object of the present invention may also be attained according to a seventh aspect of the invention, which provides a blood pressure monitor apparatus for monitoring a blood pressure of a living subject, comprising: blood pressure-relating information obtaining means for successively obtaining blood pressure-relating information which decreases with an increase of the blood pressure of the subject; abnormality judging means for judging that the blood pressure of the subject is abnormal when the blood pressure-relating information successively obtained by the obtaining means is smaller than a predetermined reference value ($TH_L$); decrease determining means for determining a decrease of the blood pressure-relating information successively obtained by the obtaining means; and reference value determining means for determining the reference value ($TH_L$) based on the decrease of the blood pressure-relating information successively obtained by the obtaining means, by utilizing a predetermined relationship between reference value and decrease of blood pressure-relating information, the relationship being predetermined such that a greater reference value ($TH_L$) corresponds to a greater decrease of blood pressure-relating information.

The above-indicated object of the present invention may also be attained according to an eighth aspect of the invention, which provides a blood pressure monitor apparatus for monitoring a blood pressure of a living subject, comprising: blood pressure-relating information obtaining means for successively obtaining blood pressure-relating information which increases with a decrease of the blood pressure of the subject; abnormality judging means for judging that the blood pressure of the subject is abnormal when the blood pressure-relating information successively obtained by the obtaining means is greater than a predetermined reference value ($TH_H$); increase determining means for determining an increase of the blood pressure-relating information successively obtained by the obtaining means; and reference value determining means for determining the reference value ($TH_H$) based on the increase of the blood pressure-relating information successively obtained by the obtaining means, by utilizing a predetermined relationship between reference value and increase of blood pressure-relating information, the relationship being predetermined such that a smaller reference value ($TH_H$) corresponds to a greater increase of blood pressure-relating information.

In a preferred form of the above fifth or seventh aspect of the present invention, the decrease is selected from the group consisting of an amount of decrease of the blood pressure-relating information and a rate of decrease of the blood pressure-relating information.

In a preferred form of the above sixth or eighth aspect of the present invention, the increase is selected from the group consisting of an amount of increase of the blood pressure-relating information and a rate of increase of the blood pressure-relating information.

In a preferred form of the above fifth or sixth aspect of the present invention, the blood pressure-relating information is selected from the group consisting of an estimated blood pressure (EBP), a pulse-wave propagation velocity ($V_M$) and a normalized pulse-wave area ($S_F$).

In a preferred form of the above seventh or eighth aspect of the present invention, the blood pressure-relating information comprises a pulse-wave propagation time (DT).

BRIEF DESCRIPTION OF THE DRAWINGS

The above and optional objects, features, and advantages of the present invention will be better understood by reading the following detailed description of the preferred embodiments of the invention when considered in conjunction with the accompanying drawings in which.

DETAILED DESCRIPTION OF THE PREFERRED EMBODIMENTS

Figure 1:
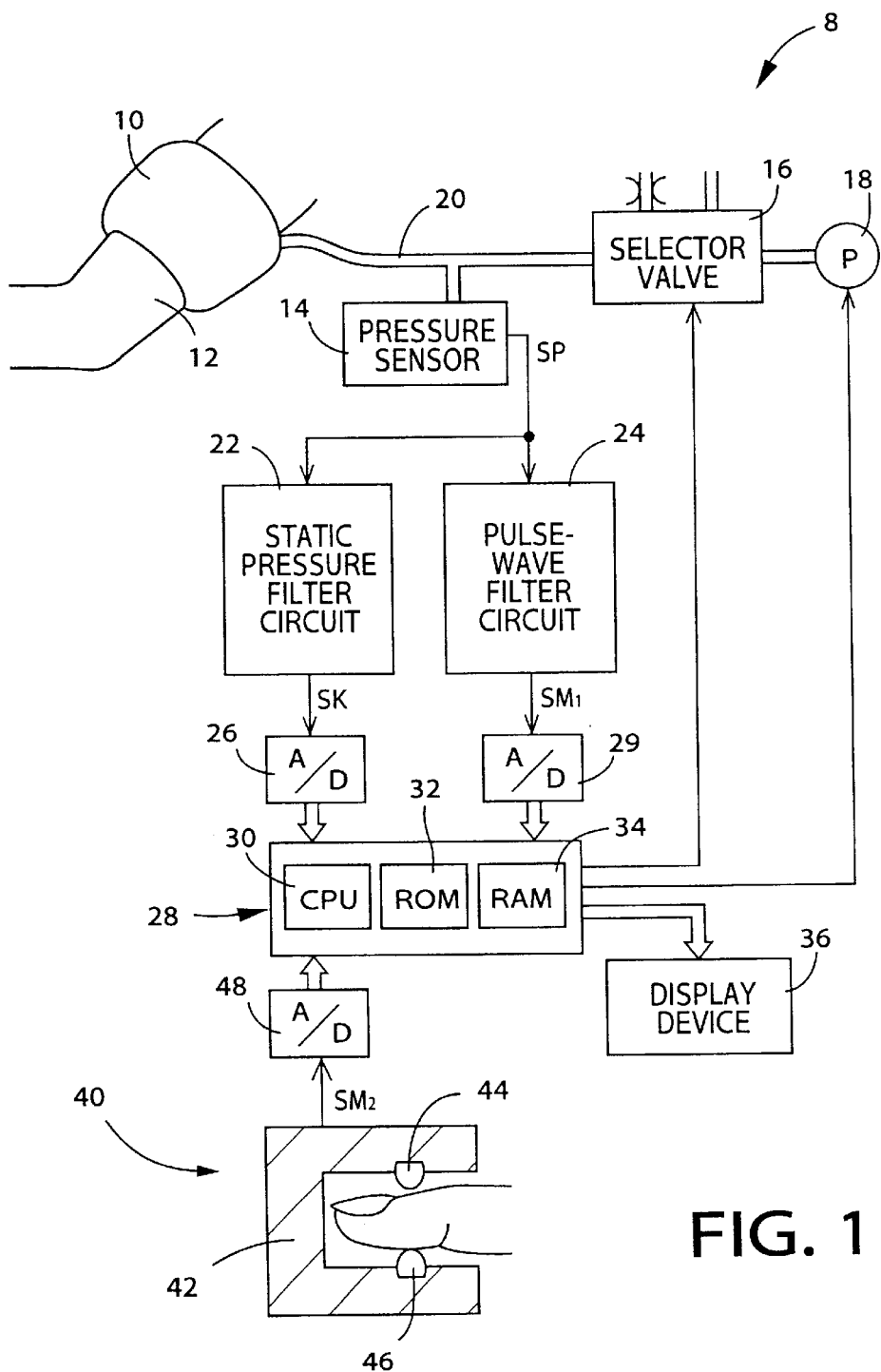
FIG. 1 is a diagrammatic view of a blood pressure monitor apparatus constructed according to one embodiment of the present invention.

Referring first to FIG. 1, there is shown a blood pressure (BP) monitor apparatus 8 constructed according to a first embodiment of the present invention. The BP monitor apparatus 8 of FIG. 1 includes an inflatable cuff 10 which has an elongate fabric bag and a rubber bag accommodated in the elongate fabric bag and which is to be wound around an upper arm 12 of a patient, for instance. A pressure sensor 14, a selector valve 16, and an air pump 18 are connected to the cuff 10 via a conduit piping 20.

The pressure sensor 14 detects an air pressure in the cuff 10 and supplies a pressure signal SP representative of the detected pressure to a static-pressure filter circuit 22 and a pulse-wave filter circuit 24. The static-pressure filter circuit 22 includes a low-pass filter and transmits a static component of the signal SP as a cuff-pressure signal SK representative of a static cuff pressure Pc to an electronic control device 28 via a first analog-to-digital (A/D) converter 26.

The pulse-wave filter circuit 24 has a band-pass filter and transmits an oscillating component of the pressure signal SP as a pulse-wave signal $SM_1$ to the electronic control device 28 via a second analog-to-digital (A/D) converter 29. The pulse-wave signal $SM_1$ represents a pulse wave, i.e., an oscillatory pressure wave which is produced from a brachial artery (not shown) of the patient in synchronism with the heartbeat of the patient and is transmitted to the cuff 10.

The electronic control device 28 is constituted by a so-called microcomputer which includes a central processing unit (CPU) 30, a read only memory (ROM) 32, a random access memory (RAM) 34, and an input and output (I/O) port not shown. The CPU 30 performs signal processing operations according to control programs stored in the ROM 32 by utilizing a temporary data storage function of the RAM 34, generates drive signals through the I/O port for controlling the selector valve 16 and the air pump 18, and outputs a display signal to a display device 36 through the I/O port.

The BP monitor apparatus 8 further includes a photoelectric pulse-wave sensor 40 which functions as a volume pulse-wave detecting device for detecting a volume pulse-wave (plethysmograph) of peripheral blood vessels of the subject. The photoelectric pulse-wave sensor 40 includes a housing 42 for accommodating a body portion (e.g., an end portion of a finger) of the living subject therein. The housing 42 is provided with a light-emitting element 44 and a light-receiving element 46 which are opposed to each other on predetermined locations of the inner surface of the housing 42. The light-emitting element 44 emits, toward the skin of the body portion accommodated in the housing 42, a red or infrared light having a wavelength which can be reflected by hemoglobin present in blood of the body portion, preferably the light having a wavelength of about 800 nm at which the light is not influenced by blood oxygen saturation. The light-receiving element 46 receives and detects the light transmitted through the body portion. The thus constructed photoelectric pulse-wave sensor 40 generates a photoelectric pulse-wave signal $SM_2$ representative of the blood volume in the blood capillaries (capillary vessels) of the body portion. The generated signal $SM_2$ is supplied to the electronic control device 28 through a third analog-to-digital (A/D) converter 48.

Figure 2:
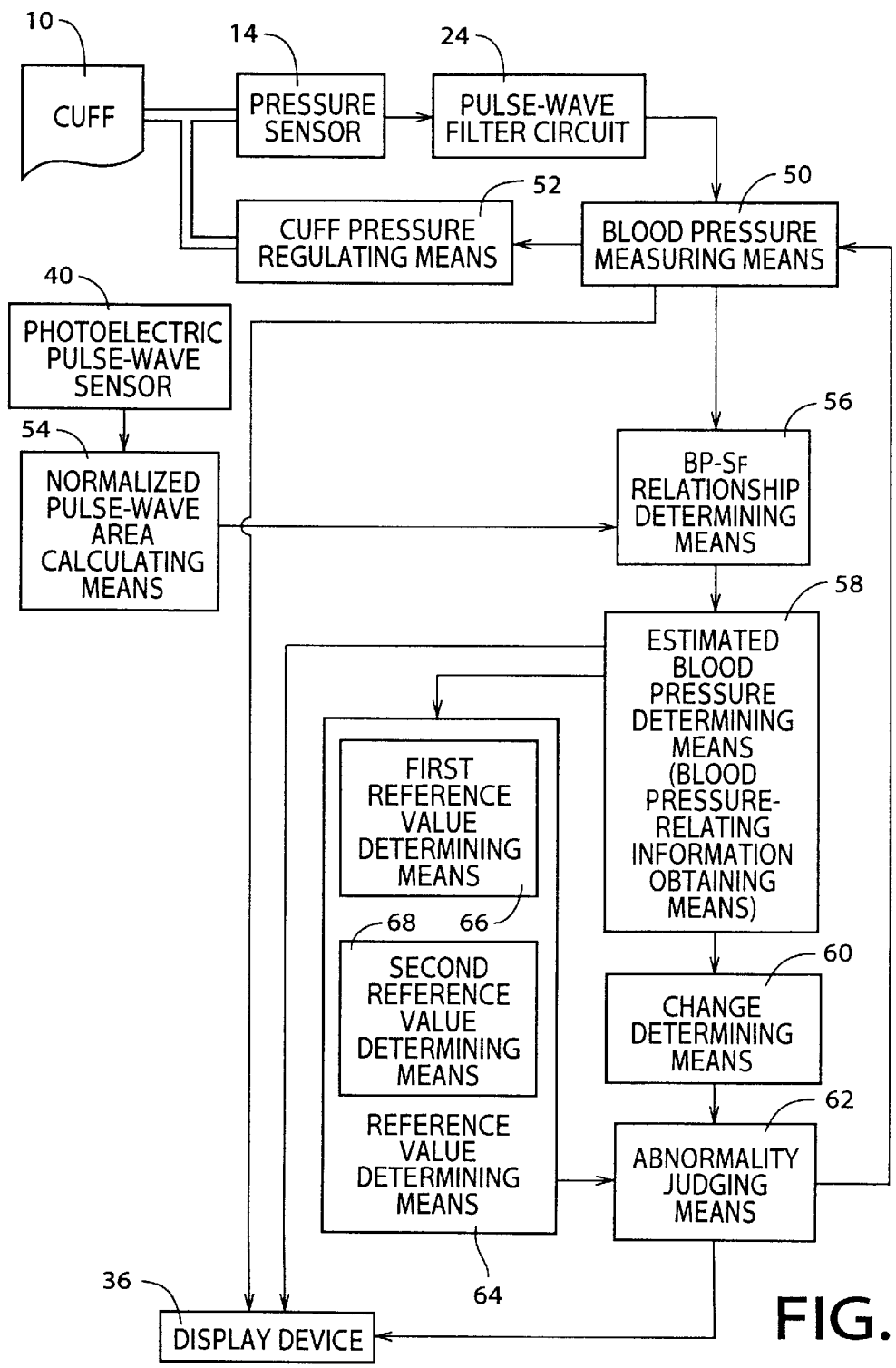
FIG. 2 is a block diagram for illustrating essential functions of an electronic control device of the apparatus of FIG. 1.

FIG. 2 illustrates essential functions of the electronic control device 28 of the BP monitor apparatus 8 of the present embodiment. The BP monitor apparatus 8 includes blood pressure (BP) measuring means 50, cuff pressure regulating means 52, normalized pulse-wave area calculating means 54, relationship determining means 56 for determining a relationship between blood pressure and normalized pulse-wave area, estimated blood pressure determining means (blood pressure-relating information obtaining means) 58, change (i.e., decrease or increase) determining means 60, abnormality judging means 62, and reference value determining means 64.

The BP measuring means 50 measures a systolic blood pressure $BP_{sys}$, a mean blood pressure $BP_{MEAN}$, and a diastolic blood pressure $BP_{DIA}$ of the subject according to a known oscillometric method. Described in detail, after the pressure in the cuff 10 wound around on the upper arm of the subject is first increased up to a predetermined target value $P_{CM}$ (e.g., about 180 mmHg) by the cuff pressure regulating means 52, the pressure in the cuff 10 is slowly lowered at a rate of about 3 mmHg/sec. The blood pressure values $BP_{sys}$, $BP_{MEAN}$, and $BP_{DIA}$ are determined on the basis of the change of respective amplitudes of successive pulses of the pulse-wave signal $SM_1$ obtained while the cuff pressure is slowly lowered. The determined blood pressure values $BP_{sys}$, $BP_{MEAN}$, and $BP_{DIA}$ are indicated on the display 36.

Figure 3:
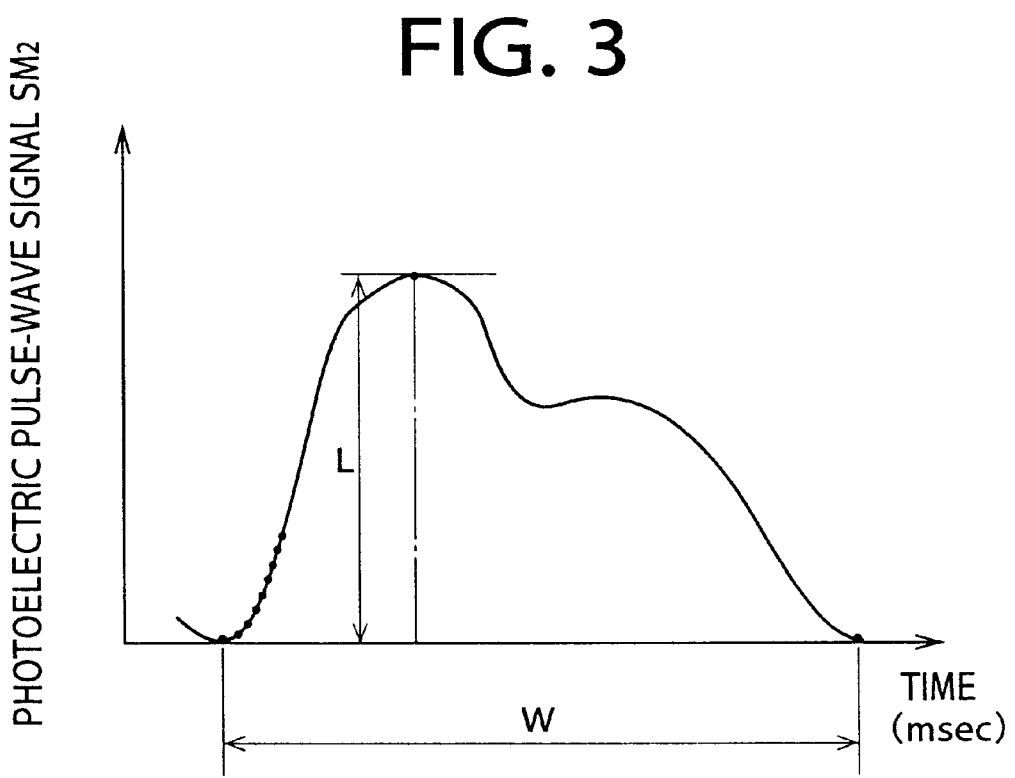
FIG. 3 is a graph explaining a photoelectric pulse wave detected by a photoelectric pulse-wave sensor of the apparatus of FIG. 1.

The normalized pulse-wave area calculating means 54 calculates an area $S_F$ which is defined by a waveform of each of successive pulses of the photoelectric pulse-wave signal $SM_2$ and is normalized based on a period W and an amplitude L of each pulse of the photoelectric pulse-wave signal $SM_2$. As shown in the graph of FIG. 3, the waveform of each pulse of the photoelectric pulse-wave signal $SM_2$ is defined by a series of data points indicative of respective instantaneous magnitudes of the photoelectric pulse-wave signal $SM_2$ which are input to the control device 28 at a predetermined interval such as several milliseconds to several tens of milliseconds. A pulse-wave area S is obtained by integrating, in the period W of the pulse of the photoelectric pulse-wave signal $SM_2$, the respective magnitudes of the pulse of the signal $SM_2$, and then the normalized pulse-wave area $S_F$ is calculated according to the following expression: $S_F=S/(W \times L)$. The normalized pulse-wave area $S_F$ is a dimensionless value indicative of a ratio of the pulse-wave area S to an area defined by the period W and the amplitude L of the each pulse of the photoelectric pulse wave. A symbol %MAP may be used in place of the symbol $S_F$.

Figure 4:
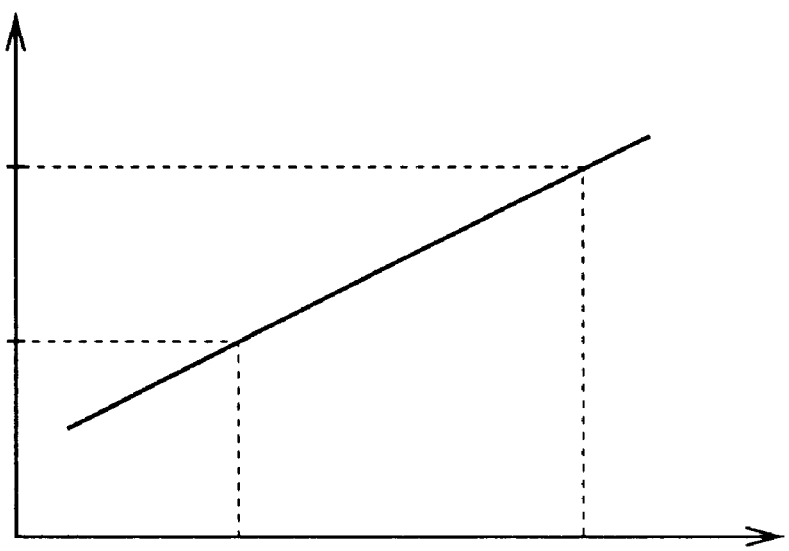
FIG. 4 is a graph showing a relationship between normalized pulse-wave area and estimated blood pressure, which relationship is used in the apparatus of FIG. 1.

The relationship determining means 56 determines a relationship between the blood pressure BP (one of the systolic, mean and diastolic blood pressure $BP_{sys}$, $BP_{MEAN}$, and $BP_{DIA}$) measured by the BP measuring means 50 and the normalized pulse-wave area $S_F$ calculated by the normalized pulse-wave area calculating means 54, when the blood pressure BP is measured by the BP measuring means 50. This relationship (hereinafter referred to as "BP-$S_F$ relationship") is indicated in the graph of FIG. 4 by way of example, and is represented by an equation: $EBP = \alpha \cdot S_F + \beta$, for instance, where $\alpha$ is a constant indicative of a gradient, $\beta$ is a constant indicative of an intercept, and EBP is an estimated blood pressure value. In the case where the BP-$S_F$ relationship represented by the equation $EBP = f(S_F)$ is determined based on one set of blood pressure BP and normalized pulse-wave area $S_F$, one of the constants $\alpha$ and $\beta$ is a statistically obtained value which is selected depending upon the sexuality and age of the subject. When the BP-$S_F$ relationship represented by the equation $EBP = f(S_F)$ is determined based on at least two sets of blood pressure BP and normalized pulse-wave area $S_F$, the constants $\alpha$ and $\beta$ in the equation are determined for each individual subject. The determined constants $\alpha$ and $\beta$ may be corrected each time a blood pressure is measured by the BP measuring means 50.

The estimated blood pressure determining means 58 functioning as the blood pressure-relating information obtaining means successively determines an estimated blood pressure EBP of the subject, based on each of the normalized pulse-wave area values $S_F$ successively calculated by the normalized pulse-wave area calculating means 54, according to the equation $EBP = f(S_F)$ determined by the BP-$S_F$ relationship determining means 56. The successively determined estimated blood pressure values EBP are indicated in a trend graph on the display device 36. When the systolic blood pressure value $BP_{sys}$ is used to determine the BP-$S_F$ relationship represented by the equation $EBP = f(S_F)$, the estimated blood pressure value EBP determined by the determining means 58 indicates the systolic blood pressure of the subject. When the mean blood pressure value $BP_{MEAN}$ is used to determine the relationship ($EBP = f(S_F)$), the value EBP indicates the mean blood pressure, while the value EBP indicates the diastolic blood pressure when the diastolic blood pressure value $BP_{DIA}$ is used to determine the relationship.

The change (i.e., decrease or increase) determining means 60 determines a change value $\Delta EBP$ of the estimated blood pressure EBP. The change value $\Delta EBP$ represents an absolute value of a change of the estimated blood pressure EBP. For instance, the change value $\Delta EBP$ is an absolute value of a rate of change or an amount of change of the currently determined estimated blood pressure value EBP from a moving blood-pressure average $EBP_{AV}$ obtained for a predetermined number of pulses (e.g., about 20 to 30 pulses) or within a predetermined time period ranging from 30 seconds to several minutes. Alternatively, the change value $\Delta EBP$ may be an absolute value of a rate of change or an amount of change of the currently determined estimated blood pressure value EBP from the estimated blood pressure value EBP obtained in the prior blood pressure measurement of the BP measuring means 50. Further, the change value $\Delta EBP$ may be an absolute value of a rate of change or an amount of change of the currently determined estimated blood pressure value EBP from the estimated blood pressure value obtained a predetermined time period (e.g., 10 minutes) before the current estimated blood pressure value EBP has been obtained, or from the estimated blood pressure value obtained for a prior pulse which has preceded the currently detected pulse by a predetermined number. The change value $\Delta EBP$ is represented as $|EBP_{AV} - EBP|$ or $|(EBP_{AV} - EBP)/EBP_{AV}|$.

The abnormality judging means 62 judges that the blood pressure of the subject is abnormal when the change value $\Delta EBP$ determined by the determining means 60 is greater than a predetermined reference value $\gamma$, in other words, if the determined change value $\gamma EBP$ is greater than at least one of a first reference value $\gamma_1$ and a second reference value $\gamma_2$ which are determined by the reference value determining means 64 including first reference value determining means 66 and second reference value determining means 68. Described more specifically, the first reference value determining means 66 successively determines a first reference value $\gamma_1$ used in judging abnormality of the blood pressure by the abnormality judging means 62, based on an estimated blood pressure EBP successively determined by the determining means 58, by utilizing a predetermined relationship between first reference value $\gamma_1$ and estimated blood pressure EBP, which relationship is predetermined such that a smaller first reference value $\gamma_1$ corresponds to a smaller estimated blood pressure EBP. The second reference value determining means 68 successively determines a second reference value $\gamma_2$ used in judging abnormality of the blood pressure of the subject by the abnormality judging means 62, based on an estimated blood pressure EBP successively determined by the determining means 58, by utilizing a predetermined relationship between second reference value $\gamma_2$ and estimated blood pressure EBP, which relationship is predetermined such that a smaller second reference value $\gamma_2$ corresponds to a greater estimated blood pressure EBP.

There will be described the operation of the electronic control device 28 referring to the flow chart of FIG. 5.

Figure 5:
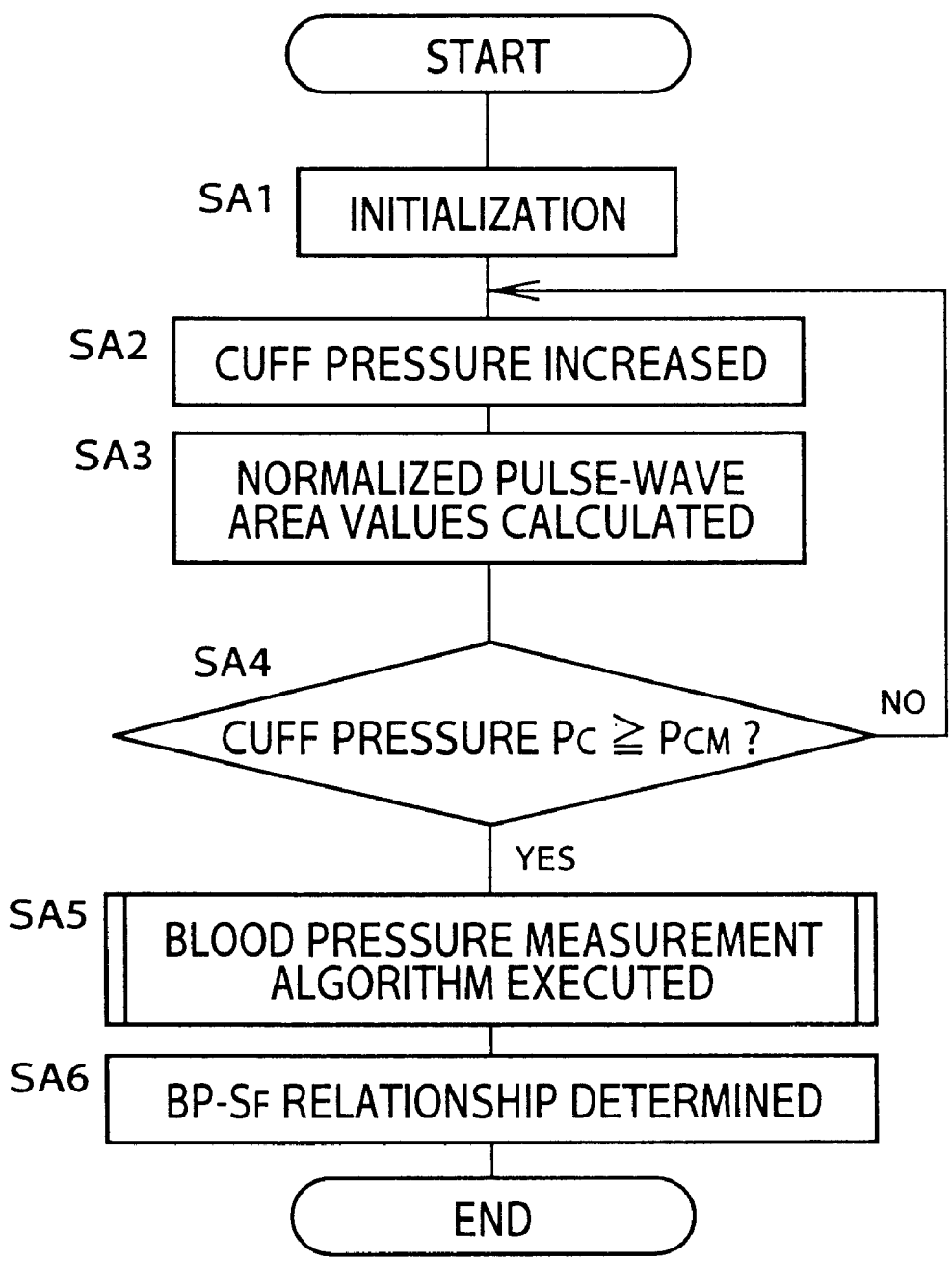
FIG. 5 is a flow chart representing a control routine for determining the relationship between the normalized pulse-wave area and the estimated blood pressure, which control routine is executed by the electronic control device of the apparatus of FIG. 1.

A control routine of FIG. 5 for determining a BP-$S_F$ relationship (a relationship between blood pressure and normalized pulse-wave area) is initiated with Step SA1 in which counters and registers (not shown) are reset. Step SA 1 is followed by Step SA2 corresponding to the cuff pressure regulating means 52 to quickly increase the cuff pressure for effecting a blood pressure measurement, by placing the selector valve 16 to its inflation position and actuating the air pump 18.

Step SA 2 is followed by Step SA3 corresponding to the normalized pulse-wave area calculating means 54. In this Step SA3, a pulse-wave area S, a period W, and an amplitude L of each pulse of the photoelectric pulse wave are obtained based on the photoelectric pulse-wave signal $SM_2$ (shown in the graph of FIG. 3) detected by the photoelectric pulse-wave sensor 40. On the basis of the obtained pulse-wave area S, period W, amplitude L of each pulse of the photoelectric pulse wave, a normalized pulse-wave area $S_F$ is calculated according to the expression $S_F = S/(W \times L)$.

The control flow then goes to Step SA4 to judge whether or not the cuff pressure $P_C$ is increased up to or higher than a predetermined target value $P_{CM}$ (e.g., 180 mmHg). If a negative decision is made in Step SA4, the control flow goes back to Step SA2 so as to continue the increasing of the cuff pressure $P_C$. If the cuff pressure $P_C$ is equal to or higher than the target value $P_{CM}$, an affirmative decision is made in Step SA4 and the control flow goes to Step SA5 corresponding to the blood pressure measuring means 50 to perform a blood pressure measuring algorithm. Described in detail, the air pump 18 is turned off and the selector valve 16 is switched from the inflation position to its slow-deflation position where the selector valve 16 permits the pressurized air to be slowly discharged from the cuff 10, so that the pressure in the cuff 10 is slowly decreased at a predetermined rate of 3 mmHg/sec. A systolic blood pressure $BP_{sys}$, a mean blood pressure $BP_{MEAN}$, and a diastolic blood pressure are determined based on the variation of amplitudes of successive pulses of the pulse wave represented by the pulse-wave signal $SM_1$ obtained during the slow decreasing of the cuff pressure, according to a well-known oscillometric blood pressure determining algorithm. Further, the pulse rate is determined based on an interval between successive adjacent two pulses of the pulse wave. The thus determined blood pressure values $BP_{sys}$, $BP_{MEAN}$, $BP_{DIA}$, and the pulse rate are indicated on the display device 36, and the selector valve 16 is switched from the slow-deflation position to its rapid-deflation position, whereby the pressure in the cuff 10 is rapidly lowered.

Step SA5 is followed by Step SA6 corresponding to the $BP-S_F$ relationship determining means 56. In this Step SA 6, the control device 28 determines a relationship between the normalized pulse-wave area $S_F$ obtained in Step SA3 corresponding to the normalized pulse-wave calculating means 54 and the blood pressure value $BP_{sys}$, $BP_{MEAN}$, $BP_{DIA}$ obtained in Step SA5 corresponding to the blood pressure measuring means 50 using the cuff 10. The relationship (represented by the expression: $EBP=\alpha \cdot S_F+\beta$) is determined based on one set of data consisting of one of the blood pressure values $BP_{sys}$, $BP_{MEAN}$, $BP_{DIA}$ obtained in Step SA5 and the normalized pulse-wave area $S_F$ obtained in Step SA3, and another set of data obtained in Steps SA5, SA3 in the prior control cycle according to the control routine of FIG. 5.

Figure 6:
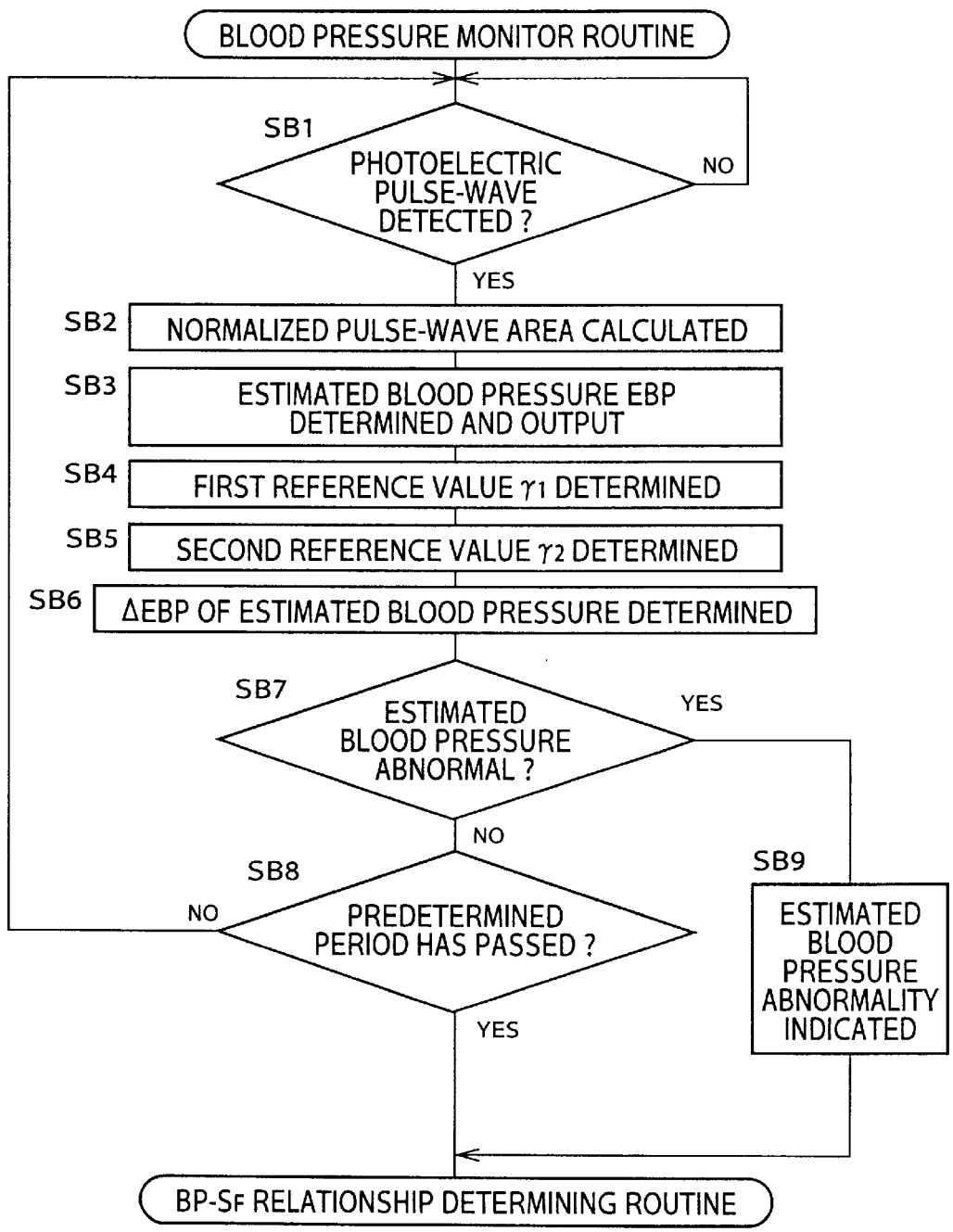
FIG. 6 is a flow chart representing a control routine for monitoring a blood pressure of the subject executed by the electronic control device of the apparatus of FIG. 1.

After the $BP-S_F$ relationship is determined as described above, the electronic control device 28 executes a blood pressure monitor routine as indicated by a flow chat of FIG. 6. The control routine of FIG. 6 is initiated with Step SB1 to judge whether or not the photoelectric pulse wave has been detected. As long as a negative judgment is made in Step SB1, this step is repeatedly implemented. If an affirmative judgment is made in Step SB1, the control flow goes to Step SB2 corresponding to the normalized pulse-wave area calculating means 54 to calculate a normalized pulse-wave area $S_F$ of a pulse of the photoelectric pulse wave read in Step SB1, in the same manner as carried out in Step SA3 of the control routine of FIG. 5.

Step SB2 is followed by Step SB3 corresponding to the estimated blood pressure determining means 58. In this Step SB3, an estimated blood pressure EBP is determined based on the normalized pulse-wave area $S_F$ calculated in Step SB2, according to the $BP-S_F$ relationship ($EBP=\alpha \cdot S_F+\beta$) determined in Step SA6 of the control routine of FIG. 5. The determined estimated blood pressure EBP is output to the display device 36 so as to indicate a trend graph of the estimated blood pressure values determined for the respective pulses of the pulse wave.

The control flow then goes to Steps SB4 and SB5 cooperating with each other to constitute the reference value determining means 64. In Step SB4 corresponding to the first reference value determining means 66, a first reference value $\gamma_1$ is determined based on the estimated blood pressure EBP determined in Step SB3, by utilizing a predetermined relationship between first reference value $\gamma_1$ and estimated blood pressure EBP, as shown in the graph of FIG. 7 (a). Described in detail, the first reference value $\gamma_1$ is predetermined such that the first reference value $\gamma_1$ linearly decreases as the estimated blood pressure value EBP obtained in Step SB3 decreases from a first empirical value $EBP_1$, and such that the first reference value $\gamma_1$ is kept at a constant value (e.g., 40%) when the estimated blood pressure EBP is higher than the first empirical value $EBP_1$.

In the following Step SB5 corresponding to the second reference value determining means 68, a second reference value $Y_2$ is determined based on the estimated blood pressure EBP determined in Step SB3, by utilizing a $\gamma_2$ predetermined relationship between second reference value $\gamma_2$ and estimated blood pressure EBP, as shown in the graph of FIG. 7 (b). Described in detail, the second reference value $\gamma_2$ is predetermined such that the second reference value $\gamma_2$ linearly decreases as the estimated blood pressure EBP obtained in Step SB3 increases form a second empirical value $EBP_2$, and such that the second reference value $\gamma_2$ is kept at a constant value (e.g., 40%) when the estimated blood pressure EBP is lower than the second empirical value $EBP_2$.

The control flow then goes to Step SB6 corresponding to the change determining means 60 to determine, as a change value $\Delta EBP$, a rate of change of the estimated blood pressure EBP determined in Step SB3 with respect to the estimated blood pressure EBP obtained in the prior blood pressure measurement using the cuff 10, in other words, the estimated blood pressure EBP determined immediately after the blood pressure value BP was measured in the prior blood pressure measuring operation using the cuff 10.

Figure 7A:
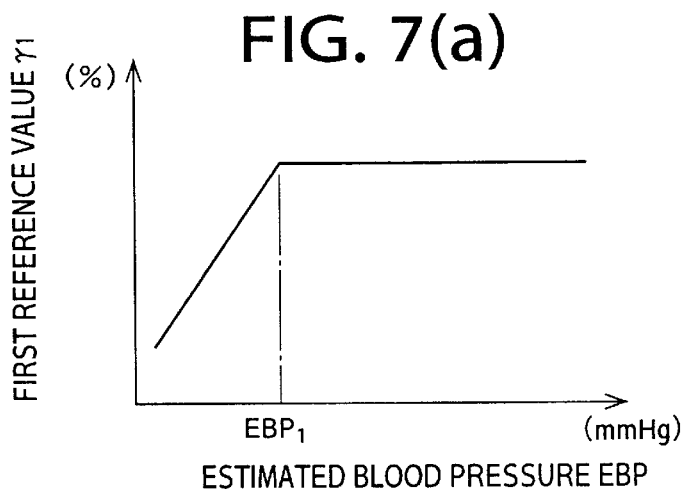
FIGS. 7(a)–(c) are graphs showing relationships between the estimated blood pressure and the first and/or second reference value.
Figure 7B:
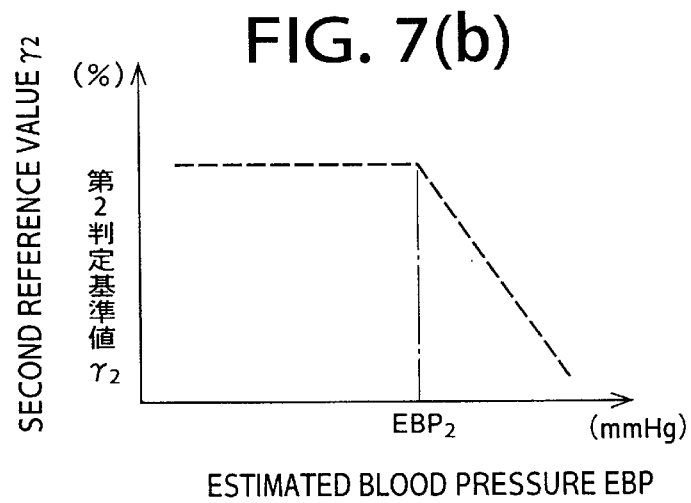
Figure 7C:
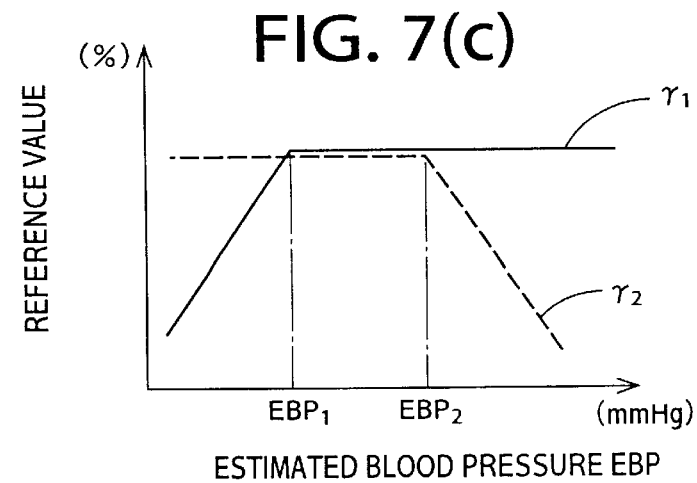

Step SB6 is followed by Step SB7 corresponding to the abnormality judging means 62 to judge whether or not the change value $\Delta EBP$ determined in Step SB6 is greater than at least one of the first reference value $\gamma_1$ determined in Step SB4 and the second reference value $\gamma_2$ determined in Step SB5. Described more specifically referring to the graph of FIG. 7(c) in which the graphs of FIGS. 7(a) and 7(b) are superimposed on each other, it is judged in Step SB7 whether or not the change value $\Delta EBP$ determined in Step SB6 is greater than the first reference value $\gamma_1$ when the estimated blood pressure EBP determined in Step SB3 is lower than the first empirical value $EBP_1$, whether or not the change value $\Delta EBP$ determined in Step SB6 is greater than the first reference value $\gamma_1$, namely, the second reference value $\gamma_2$, when the estimated blood pressure EBP determined in Step SB3 is higher than the first empirical value $EBP_1$ and lower than the second empirical value $EBP_2$, and whether or not the change value $\Delta EBP$ calculated in Step SB6 is greater than the second reference value $\gamma_2$ when the estimated blood pressure EBP is higher than the second empirical value $EBP_2$.

If a negative judgment is made in Step SB7, the control flow goes to Step SB8 to judge whether or not a predetermined period (e.g., 15 to 20 minutes), that is, a calibration period, has passed after the control routine of FIG. 5 for determining the $BP-S_F$ relationship was performed. If a negative judgment is made in Step SB8, the control flow goes back to Step SB1 and the following steps so as to repeat the blood pressure monitor routine, that is, successively determine the estimated blood pressure EBP for each of the pulses, and timewise indicate the trend graph of the determined estimated blood pressure values EBP on the display device 36.

On the other hand, if an affirmative judgment is made in Step SB7, the control flow goes to Step SB9 to indicate abnormality of the blood pressure on the display device 36, and implement the control routine of FIG. 5 for updating the BP-$S_F$ relationship, in order to perform a reliable blood pressure measurement by using the cuff 10, and determine a new BP-$S_F$ relationship (EBP=$\alpha \cdot S_F + \beta$).

In the present embodiment explained above, the change determining means 60 (Step SB6) determines the change value $\Delta$EBP of the estimated blood pressure EBP successively determined by the estimated blood pressure determining means 58 (Step SB3). The abnormality judging means 62 (Step SB7) judges that the blood pressure of the subject is abnormal when the change value $\Delta$EBP determined by the change determining means 60 (Step SB6) is greater than at least one of the first and second reference values $\gamma_1$ and $\gamma_2$. In other words, the abnormality judging means 62 judges the abnormality of the blood pressure of the subject when the estimated blood pressure EBP has abruptly changed even if the estimated blood pressure EBP is a relatively normal value. According to this arrangement, the abnormality of the blood pressure of the subject can be quickly detected without delay when the blood pressure has abruptly changed.

In the present embodiment, the first reference value determining means 66 (SB4) determines the first reference value $\gamma_1$ used by the abnormality judging means 62 (Step SB7) for judging the abnormality of the blood pressure, such that a smaller first reference value $\gamma_1$ corresponds to a smaller estimated blood pressure value EBP determined by the estimated blood pressure determining means 58 (SB3) In the present arrangement, when the blood pressure of the subject is relatively low, the abnormality of the blood pressure is detected even when the change value $\Delta$EBP is relative small. On the other hand, when the blood pressure of the subject is not so low, the abnormality of the blood pressure is detected only when the change value $\Delta$EBP is relatively large. Accordingly, the present arrangement permits the determination of abnormal blood pressure without delay when the blood pressure has abruptly changed, and eliminates the determination of abnormal blood pressure when the blood pressure of the subject is not so low.

In the present embodiment, the second reference value determining means 68 (SB5) determines the second reference value $\gamma_2$ used by the abnormality judging means 62 (Step SB7) for judging the abnormality of the blood pressure, such that a smaller second reference value $\gamma_2$ corresponds to a greater estimated blood pressure EBP determined by the estimated blood pressure determined means 58 (SB3). In the present arrangement, when the blood pressure of the subject is relatively high, the abnormality of the blood pressure is detected even when the change value $\Delta$EBP is relative small. On the other hand, when the blood pressure of the subject is not so high, the abnormality of the blood pressure is detected only when the change value $\Delta$EBP is relatively large. Accordingly, the present arrangement permits the determination of abnormal blood pressure without delay when the blood pressure has abruptly changed, and eliminates the determination of abnormal blood pressure when the blood pressure of the subject is not so high.

Figure 8:
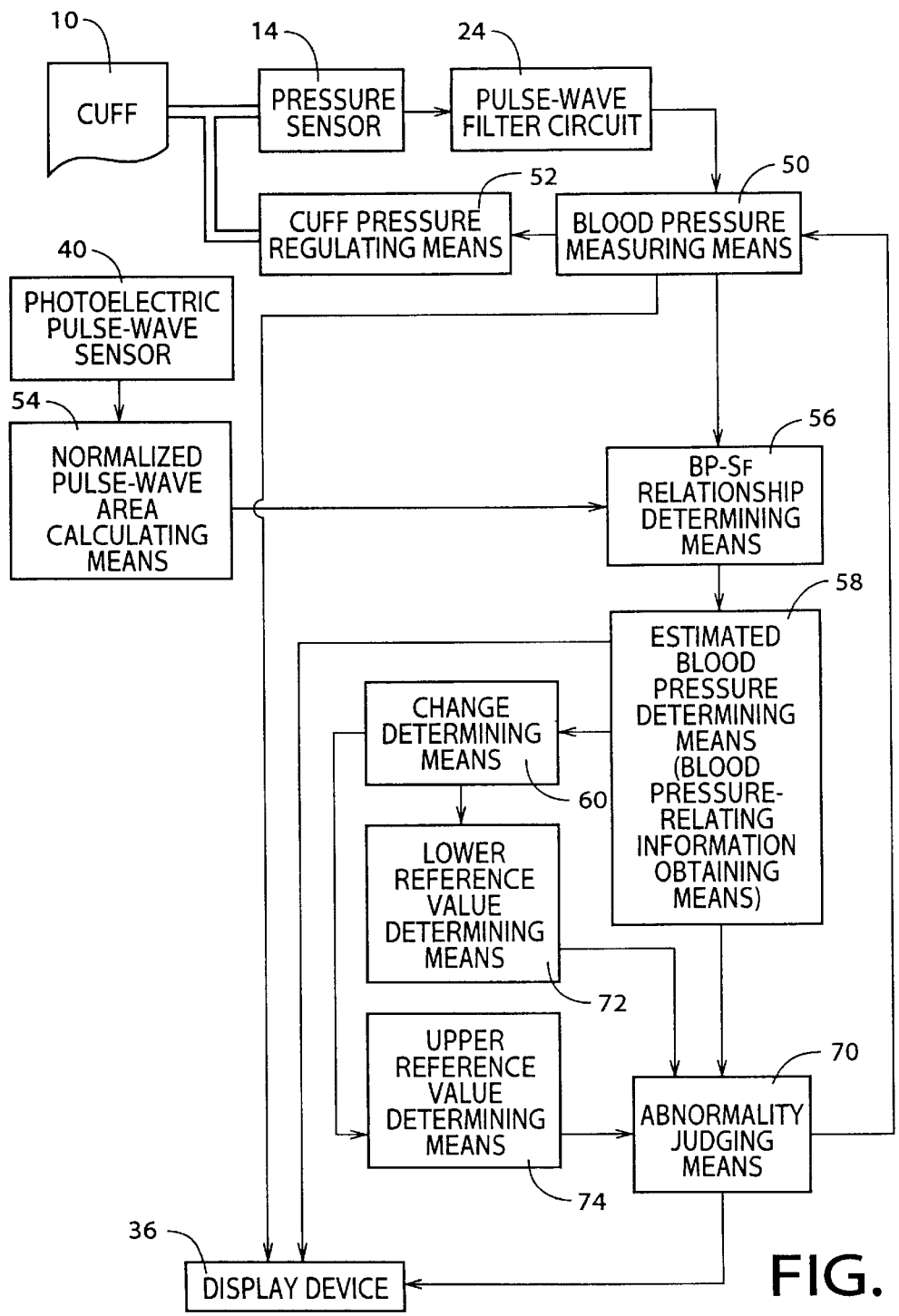
FIG. 8 is a diagrammatic view of a blood pressure monitor apparatus constructed according to another embodiment of the present invention.

Referring next to FIG. 8, there will be described a second embodiment of the present invention. In this second embodiment, the same reference numerals as used in the previous first embodiment are used to identify the corresponding components and the detailed explanation thereof is dispensed with.

FIG. 8 is a block diagram for explaining essential functions of an electronic control device 28 of a BP monitor apparatus as the second embodiment. The BP monitor apparatus of this second embodiment has the same hardware construction and control circuit as those of the BP monitor apparatus according to the first embodiment shown in FIG. 1, except that abnormality judging means 70 in the second embodiment is different from that in the first embodiment as described below.

In FIG. 8, the abnormality judging means 70 judges that the blood pressure of the subject is abnormal when the estimated blood pressure EBP successively determined by the estimated blood pressure determining means 58 is smaller than a predetermined lower reference value $TH_L$ or greater than a predetermined upper reference value $TH_H$.

Described more specifically, a lower reference value determining means 72 successively determines a lower reference value $TH_L$ used by the abnormality judging means 70 for judging abnormality of the blood pressure of the subject, based on a change value $\Delta$EBP of the estimated blood pressure, i.e., an absolute value of a change of the estimated blood pressure EBP, determined by the change (i.e., decrease or increase) determining means 60, by utilizing a predetermined relationship between lower reference value $TH_L$ and change value $\Delta$EBP, which relationship is predetermined such that a greater lower reference value $TH_L$ corresponds to a greater change value $\Delta$EBP. On the other hand, an upper reference value determining means 74 successively determines an upper reference value $TH_H$ used by the abnormality judging means 70 for judging abnormality of the blood pressure of the subject, based on a change value $\Delta$EBP of the estimated blood pressure, i.e., an absolute value of a change of the estimated blood pressure EBP, determined by the change determining means 60, by utilizing a predetermined relationship between upper reference value $TH_H$ and change value $\Delta$EBP, which relationship is predetermined such that a smaller upper reference value $TH_H$ corresponds to a greater change value $\Delta$EBP.

Figure 9:
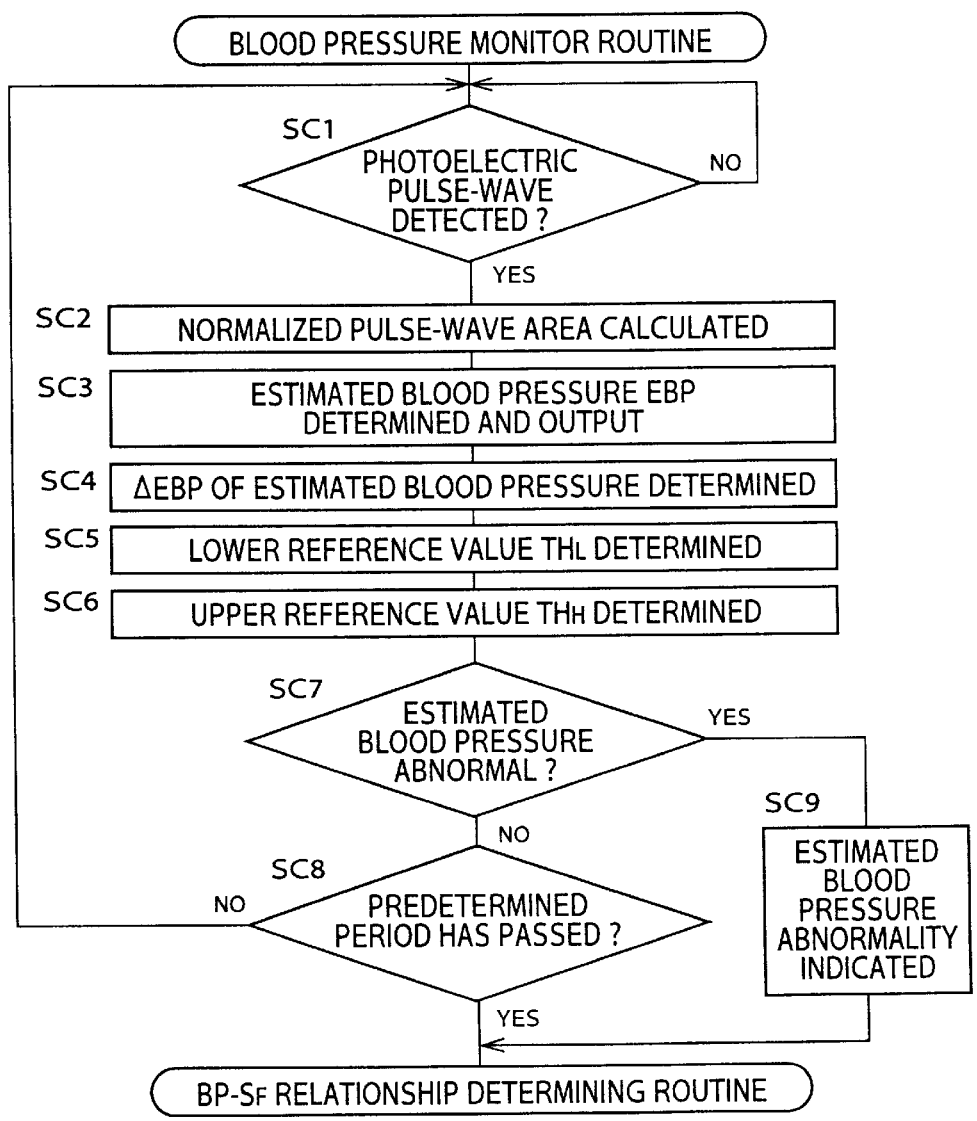
FIG. 9 is a flow chart representing a control routine for monitoring the blood pressure of the subject executed by the electronic control device of the apparatus of FIG. 8.

The electronic control device 28 of the BP monitor apparatus in the second embodiment executes a blood pressure monitor routine as shown in a flow chart of FIG. 9. In Steps SC1 through Steps SC3, the same operation as executed in Steps SB1 through SB3 of FIG. 6 is implemented so as to determine an estimated blood pressure EBP for each pulse and to output the determined estimated blood pressure EBP to the display device 36. The control flow then goes to Step SC4 corresponding to the change determining means 60 to determine a change value $\Delta$EBP in a manner similar to that in Step SB6 of FIG. 6, namely, a rate of change of the estimated blood pressure EBP determined in Step SC3 with respect to the estimated blood pressure EBP obtained in the prior blood pressure measurement by using the cuff 10.

Figure 10:
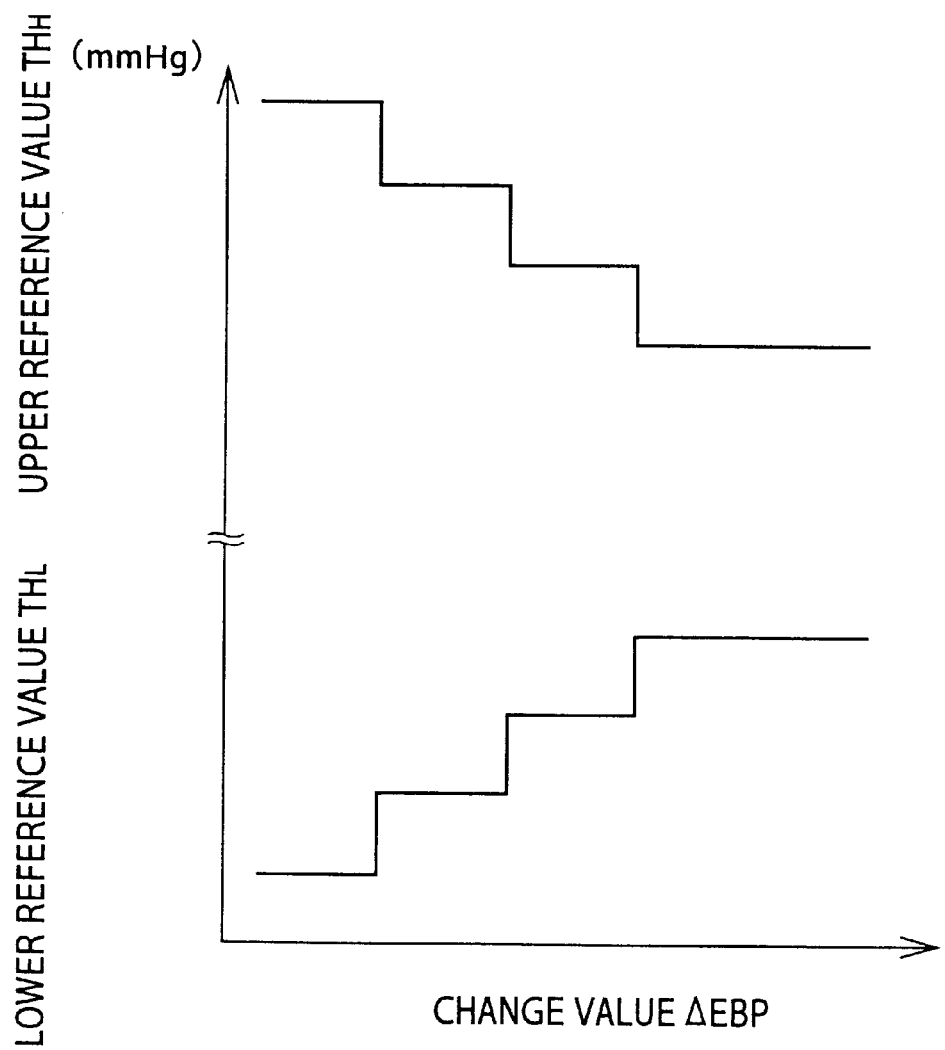
FIG. 10 is a graph showing relationships between the decrease of the blood pressure-relating information and the lower reference value ($TH_L$), and between the increase of the blood pressure-relating information and the upper reference value ($TH_H$), which relationships are used in the apparatus of FIG. 8.

Step SC 4 is followed by Step SC5 corresponding to the lower reference value determining means 72 to determine a lower reference value $TH_L$ based on the change value $\Delta$EBP determined in Step SC4, by utilizing the predetermined relationship between lower reference value $TH_L$ and change value $\Delta$EBP, as indicated in the graph of FIG. 10. The relationship shown in the graph of FIG. 10 is empirically determined such that the lower reference value $TH_L$ increases in steps with the increase of the change value $\Delta$EBP. While the lower reference value $TH_L$ changes in four steps in the present embodiment, the value $TH_L$ may change in a different number of steps.

Step SC5 is followed by Step SC6 corresponding to the upper reference value determining means 74 to determine an upper reference value $TH_H$ based on the change value $\Delta$EBP determined in Step SC4, by utilizing the predetermined relationship between upper reference value $TH_H$ and change value $\Delta EBP$, as also indicated in the graph of FIG. 10. The relationship shown in the graph of FIG. 10 is empirically determined such that the upper reference value $TH_H$ decreases in steps with the increase of the change value $\Delta EBP$. The upper reference value $TH_H$ may also change in a different number of steps.

The control flow then goes to Step SC7 corresponding to the abnormality judging means 70 to judge whether or not the estimated blood pressure EBP determined in Step SC3 is smaller than the lower reference value $TH_L$ or greater than the upper reference value $TH_H$.

If a negative judgment is made in Step SC7, the control flow goes to Step SC8 to implement the same operation as in Step SB 8 of FIG. 6, namely, to judge whether or not a predetermined calibration period has passed. If a negative judgment is made in Step SC8, the control flow goes back to Step SC1 and the following steps to repeatedly implement the blood pressure monitor routine. If an affirmative judgment is made in Step SC8, the control routine (FIG. 5) for determining the BP–$S_F$ relationship is executed to determine a new BP–$S_F$ relationship. When an affirmative judgment is made in Step SC7, the control flow goes to Step SC9 to control the display device 36 to indicate the abnormality of the blood pressure of the subject. Described in detail, if it is judged in Step SC7 that the estimated blood pressure EBP is smaller than the lower reference value $TH_L$, characters or symbols indicative of the abnormal decrease of the blood pressure of the subject are indicated on the display device 36. On the other hand, if it is judged in Step SC7 that the estimated blood pressure EBP is greater than the upper reference value $TH_H$, characters or symbols indicative of the abnormal increase of the blood pressure of the subject are indicated on the display device 36. After Step SC9 is implemented, the BP–$S_F$ relationship determining routine of FIG. 5 is implemented again for performing a reliable blood pressure measuring operation using the cuff 10 and for determining a new BP–$S_F$ relationship (EBP=$\alpha \cdot S_F + \beta$).

In the present embodiment described above, the lower reference value determining means 72 (SC5) determines the lower reference value $TH_L$ used in judging abnormal blood pressure by the abnormality determining means 70 (SC7), based on the change value $\Delta EBP$ successively determined by the change determining means 60 (SC4), by utilizing the relationship predetermined such that a greater lower reference value $TH_L$ corresponds to a greater change value $\Delta EBP$. The abnormality judging means 70 (SC7) judges that the blood pressure of the subject has abnormally decreased when the estimated blood pressure EBP successively determined by the estimated blood pressure determining means 58 (SC3) is smaller than the lower reference value $TH_L$ determined by the lower reference value determining means 72 (SC5). According to this arrangement wherein a greater lower reference value $TH_L$ corresponds to a greater change value $\Delta EBP$ of the estimated blood pressure, the abnormality judging means judges abnormality of the blood pressure of the subject without delay when the blood pressure has abruptly decreased. In addition, since a smaller lower reference value $TH_L$ corresponds to a smaller change value $\Delta EBP$ of the estimated blood pressure, the present arrangement prevents determination of abnormality of the blood pressure when the blood pressure of the subject is not so low and the blood pressure gradually decreases.

In the present embodiment described above, the upper reference value determining means 74 (SC6) determines the upper reference value $TH_H$ used in judging abnormal blood pressure by the abnormality determining means 70 (SC7), based on the change value $\Delta EBP$ successively determined by the change determining means 60 (SC4), by utilizing the relationship predetermined such that a smaller upper reference value $TH_H$ corresponds to a greater change value $\Delta EBP$. The abnormality judging means 70 (SC7) judges that the blood pressure of the subject has abnormally increased when the estimated blood pressure EBP successively determined by the estimated blood pressure determining means 58 (SC3) is greater than the upper reference value $TH_H$ determined by the upper reference value determining means 74 (SC6). According to this arrangement wherein a smaller upper reference value $TH_H$ corresponds to a greater change value $\Delta EBP$, the abnormality judging means judges abnormality of the blood pressure of the subject without delay when the blood pressure has abruptly increased. In addition, since a greater upper reference value $TH_H$ corresponds to a smaller change value $\Delta EBP$ of the estimated blood pressure, the present arrangement prevents determination of abnormality of the blood pressure when the blood pressure of the subject is not so high and the blood pressure gradually increases.

While the present invention has been described in its presently preferred embodiments, it is to be understood that the invention may be otherwise modified.

In the illustrated embodiments, the estimated pressure EBP determined based on the normalized pulse-wave area $S_F$ is used as the blood pressure-relating information. Other parameters may be employed as the blood pressure-relating information such as the normalized pulse-wave area $S_F$ and a pulse-wave propagation time DT during which a pulse wave propagates between predetermined two portions of an artery of a living subject.

If the previously described pulse-wave propagation velocity $V_M$ or the normalized pulse-wave area $S_F$ which decreases with a decrease of the blood pressure and which increases with an increase of the blood pressure is employed as the blood pressure-relating information, for instance, the first and second reference values $\gamma_1$ and $\gamma_2$ used in determining the abnormal blood pressure in the first embodiment, and the lower and upper reference values $TH_L$ and $TH_H$ used in determining the abnormal blood pressure in the second embodiment are determined as follows: Namely, in the first embodiment, the first reference value determining means 66 determines the first reference value $\gamma_1$ such that a smaller first reference value $\gamma_1$ corresponds to a smaller blood pressure-relating information $V_M$ or $S_F$, while the second reference value determining means 68 determines the second reference value $\gamma_2$ such that a smaller second reference value $\gamma_2$ corresponds to a greater blood pressure-relating information $V_M$ or $S_F$. In the second embodiment, the lower reference determining means 72 determines the lower reference value $TH_L$ such that a greater lower reference value $TH_L$ corresponds to a greater change value of the blood pressure-relating information $V_M$ or $S_F$, while the upper reference determining means 74 determines the upper reference value $TH_H$ such that a smaller upper reference value $TH_H$ corresponds to a greater change value of the blood pressure-relating information $V_M$ or $S_F$.

On the contrary, if the pulse-wave propagation time DT which increases with a decrease of the blood pressure and which decreases with an increase of the blood pressure is employed as the blood pressure-relating information, for instance, the first and second reference values $\gamma_1$ and $\gamma_2$ used in determining the abnormal blood pressure in the first embodiment, and the lower and upper reference values $TH_L$ and $TH_H$ used in determining the abnormal blood pressure in the second embodiment are determined as follows: Namely, in the first embodiment, the first reference value determining means 66 determines the first reference value $\gamma_1$ such that a smaller first reference value $\gamma_1$, corresponds to a greater blood pressure-relating information DT, while the second reference value determining means 68 determines the second reference value $\gamma_2$ such that a smaller second reference value $\gamma_2$ corresponds to a smaller blood pressure-relating information DT. In the second embodiment, the lower reference determining means 72 determines the lower reference value $TH_L$ such that a greater lower reference value $TH_L$ corresponds to a greater change value of the blood pressure-relating information DT, while the upper reference determining means 74 determines the upper reference value $TH_H$ such that a smaller upper reference value $TH_H$ corresponds to a greater change value of the blood pressure-relating information DT.

The BP monitor apparatus in each of the illustrated first and second embodiments controls the display device 36 to indicate abnormality of the blood pressure of the subject, and to effect the blood pressure measurement by the blood pressure measuring means 50 (SA5) when the abnormality judging means 62 (SB7) or 70 (SC7) judges abnormality of the blood pressure. However, the BP monitor apparatus may be modified to effect only one of the indication of abnormality of the blood pressure on the display device 36 and the blood pressure measurement by the blood pressure measuring means 50 (SA5).

While both of the first and second reference values $\gamma_1$ and $\gamma_2$ are used in judging the abnormality of the blood pressure by the abnormality judging means 62 (SB7) in the illustrated first embodiment, only one of the first and second reference values $\gamma_1$ and $\gamma_2$ may be employed.

In the illustrated second embodiment, the abnormal decrease or abnormal increase of the blood pressure of the subject is judged by the abnormality judging means 70 (SC7) using the lower and upper reference values $TH_L$ and $TH_H$. However, only one of the lower and upper reference values $TH_L$ and $TH_H$ may be used.

Although the first and second reference values $\gamma_1$ and $\gamma_2$ in the illustrated first embodiment and the lower and upper reference values $TH_L$ and $TH_H$ in the illustrated second embodiment are determined for each of the pulses, these values may be determined for every predetermined number of pulses not less than two.

It is to be understood that the present invention may be embodied with other changes, modifications, and improvements that may occur to those skilled in the art without departing from the scope of the invention defined in the attached claims.

What is claimed is:

1. A blood pressure monitor apparatus for monitoring a blood pressure of a living subject, comprising:

blood pressure-relating information obtaining means for obtaining, successively in synchronization with a heartbeat of the subject, blood pressure-relating information which decreases with a decrease of the blood pressure of the subject and which comprises at least one of an estimated blood pressure (EBP), a normalized pulse-wave area ($S_F$), and a pulse-wave propagating velocity ($V_M$);

decrease determining means for determining a decrease of the blood pressure-relating information obtained by said obtaining means successively in synchronization with the heartbeat of the subject;

abnormality judging means for judging that the blood pressure of the subject is abnormal when said decrease of the blood pressure-relating information is greater than a predetermined reference value ($\gamma_1$); and a reference value determining means for determining said reference value ($\gamma_1$) based on the blood pressure-relating information successively obtained by said obtaining means, by utilizing a predetermined relationship between said reference value and said blood pressure-relating information, said relationship being predetermined such that a smaller reference value corresponds to blood pressure-relating information corresponding to a lower blood pressure.

2. A blood pressure monitor apparatus according to claim 1, wherein said decrease is selected from the group consisting of an amount of decrease of the blood pressure-relating information and a rate of decrease of the blood pressure-relating information.

3. A blood pressure monitor apparatus for monitoring a blood pressure of a living subject, comprising:

blood pressure-relating information obtaining means for obtaining, successively in synchronization with a heartbeat of the subject, blood pressure-relating information which increases with an increase of the blood pressure of the subject and which comprises at least one of an estimated blood pressure (EBP), a normalized pulse-wave area ($S_F$), and a pulse-waving propagating velocity ($V_M$);

increase determining means for determining an increase of the blood pressure-relating information obtained by said obtaining means successively in synchronization with the heartbeat of the subject;

abnormality judging means for judging that the blood pressure of the subject is abnormal when said increase of the blood pressure-relating information is greater than a predetermined reference value ($\gamma_2$); and reference value determining means for determining said reference value ($\gamma_2$) based on the blood pressure-relating information successively obtained by said obtaining means, by utilizing a predetermined relationship between said reference value and said blood pressure-relating information, said relationship being predetermined such that a smaller reference value corresponds to blood pressure-relating information corresponding to a higher blood pressure.

4. A blood pressure monitor apparatus according to claim 3, wherein said increase is selected from the group consisting of an amount of increase of the blood pressure-relating information and a rate of increase of the blood pressure-relating information.

5. A blood pressure monitor apparatus for monitoring a blood pressure of a living subject, comprising:

blood pressure-relating information obtaining means for obtaining, successively in synchronization with a heartbeat of the subject, blood pressure-relating information which decreases with an increase of the blood pressure of the subject and which comprises a pulse-wave propagation time (DT);

decrease determining means for determining a decrease of the blood pressure-relating information obtained by said obtaining means successively in synchronization with the heartbeat of the subject;

abnormality judging means for judging that the blood pressure of the subject is abnormal when said decrease of the blood pressure-relating information is greater than a predetermined reference value ($\gamma_2$); and reference value determining means for determining said reference value ($\gamma_2$) based on the blood pressure-relating information successively obtained by said obtaining means, by utilizing a predetermined relationship between said reference value and said blood pressure-relating information, said relationship being predetermined such that a smaller reference value corresponds to blood pressure-relating information corresponding to a higher blood pressure.

6. A blood pressure monitor apparatus according to claim 5, wherein said decrease is selected from the group consisting of an amount of decrease of the blood pressure-relating information and a rate of decrease of the blood pressure-relating information.

7. A blood pressure monitor apparatus for monitoring a blood pressure of a living subject, comprising:

blood pressure-relating information obtaining means for obtaining, successively in synchronization with a heartbeat of the subject, blood pressure-relating information which increases with a decrease of the blood pressure of the subject and which comprises a pulse-wave propagation time (DT);

increase determining means for determining an increase of the blood pressure-relating information obtained by said obtaining means successively in synchronization with the heartbeat of the subject;

abnormality judging means for judging that the blood pressure of the subject is abnormal when said increase of the blood pressure-relating information is greater than a predetermined reference value ($\gamma_1$); and reference value determining means for determining said reference value ($\gamma_1$) based on the blood pressure-relating information successively obtained by said obtaining means, by utilizing a predetermined relationship between said reference value and said blood pressure-relating information, said relationship being predetermined such that a smaller reference value corresponds to blood pressure-relating information corresponding to a lower blood pressure.

8. A blood pressure monitor apparatus according to claim 7, wherein said increase is selected from the group consisting of an amount of increase of the blood pressure-relating information and a rate of increase of the blood pressure-relating information.

9. A blood pressure monitor apparatus for monitoring a blood pressure of a living subject, comprising:

blood pressure-relating information obtaining means for successively obtaining blood pressure-relating information which decreases with a decrease of the blood pressure of the subject;

abnormality judging means for judging that the blood pressure of the subject is abnormal when the blood pressure-relating information successively obtained by said obtaining means is smaller than a predetermined reference value ($TH_L$);

decrease determining means for determining a decrease of the blood pressure-relating information successively obtained by said obtaining means; and reference value determining means for determining said reference value ($TH_L$) based on said decrease of the blood pressure-relating information successively obtained by said obtaining means, by utilizing a predetermined relationship between reference value and decrease of blood pressure-relating information, said relationship being predetermined such that a greater reference value ($TH_L$) corresponds to a greater decrease of blood pressure-relating information.

10. A blood pressure monitor apparatus according to claim 9, wherein said decrease is selected from the group consisting of an amount of decrease of the blood pressure-relating information and a rate of decrease of the blood pressure-relating information.

11. A blood pressure monitor apparatus according to claim 9, wherein said blood pressure-relating information is selected from the group consisting of an estimated blood pressure, a pulse-wave propagation velocity and a normalized pulse-wave area.

12. A blood pressure monitor apparatus for monitoring a blood pressure of a living subject, comprising:

blood pressure-relating information obtaining means for successively obtaining blood pressure-relating information which increases with an increase of the blood pressure of the subject;

abnormality judging means for judging that the blood pressure of the subject is abnormal when the blood pressure-relating information successively obtained by said obtaining means is greater than a predetermined reference value ($TH_H$);

increase determining means for determining an increase of the blood pressure-relating information successively obtained by said obtaining means; and reference value determining means for determining said reference value ($TH_H$) based on said increase of the blood pressure-relating information successively obtained by said obtaining means, by utilizing a predetermined relationship between reference value and increase of blood pressure-relating information, said relationship being predetermined such that a smaller reference value ($TH_H$) corresponds to a greater increase of blood pressure-relating information.

13. A blood pressure monitor apparatus according to claim 12, wherein said increase is selected from the group consisting of an amount of increase of the blood pressure-relating information and a rate of increase of the blood pressure-relating information.

14. A blood pressure monitor apparatus according to claim 12, wherein said blood pressure-relating information is selected from the group consisting of an estimated blood pressure, a pulse-wave propagation velocity and a normalized pulse-wave area.

15. A blood pressure monitor apparatus for monitoring a blood pressure of a living subject, comprising:

blood pressure-relating information obtaining means for successively obtaining blood pressure-relating information which decreases with an increase of the blood pressure of the subject;

abnormality judging means for judging that the blood pressure of the subject is abnormal when the blood pressure-relating information successively obtained by said obtaining means is smaller than a predetermined reference value ($TH_L$);

decrease determining means for determining a decrease of the blood pressure-relating information successively obtained by said obtaining means; and reference value determining means for determining said reference value ($TH_L$) based on said decrease of the blood pressure-relating information successively obtained by said obtaining means, by utilizing a predetermined relationship between reference value and decrease of blood pressure-relating information, said relationship being predetermined such that a greater reference value ($TH_L$) corresponds to a greater decrease of blood pressure-relating information.

16. A blood pressure monitor apparatus according to claim 15, wherein said decrease is selected from the group consisting of an amount of decrease of the blood pressure-relating information and a rate of decrease of the blood pressure-relating information.

17. A blood pressure monitor apparatus according to claim 15 wherein said blood pressure-relating information comprises a pulse-wave propagation time.

18. A blood pressure monitor apparatus for monitoring a blood pressure of a living subject, comprising:

blood pressure-relating information obtaining means for successively obtaining blood pressure-relating information which increases with a decrease of the blood pressure of the subject;

abnormality judging means for judging that the blood pressure of the subject is abnormal when the blood pressure-relating information successively obtained by said obtaining means is greater than a predetermined reference value ($TH_H$);

increase determining means for determining an increase of the blood pressure-relating information successively obtained by said obtaining means; and reference value determining means for successively determining said reference value ($TH_H$) based on said increase of the blood pressure-relating information successively obtained by said obtaining means, by utilizing a predetermined relationship between reference value and increase of blood pressure-relating information, said relationship being predetermined such that a smaller reference value ($TH_H$) corresponds to a greater increase of blood pressure-relating information.

19. A blood pressure monitor apparatus according to claim 18, wherein said increase is selected from the group consisting of an amount of increase of the blood pressure-relating information and a rate of increase of the blood pressure-relating information.

20. A blood pressure monitor apparatus according to claim 18, wherein the blood pressure-relating information comprises a pulse-wave propagation time.

* * * * *